(12) United States Patent
Lin et al.

(10) Patent No.: US 9,645,078 B1
(45) Date of Patent: May 9, 2017

(54) QUANTITATIVE MICRO-VOLUME NUCLEIC ACID DETECTION DEVICE

(71) Applicant: MaestroGen Inc., Hsinchu (TW)

(72) Inventors: Sheng-Feng Lin, Hsinchu (TW); Chong-Jing Peng, Hsinchu (TW)

(73) Assignee: MaestroGen Inc., Hsinchu (TW)

( * ) Notice: Subject to any disclaimer, the term of this patent is extended or adjusted under 35 U.S.C. 154(b) by 0 days.

(21) Appl. No.: 15/067,583

(22) Filed: Mar. 11, 2016

(30) Foreign Application Priority Data

Jan. 25, 2016 (TW) .............................. 105102261 A

(51) Int. Cl.
*G01N 21/00* (2006.01)
*G01N 21/33* (2006.01)

(52) U.S. Cl.
CPC ....... *G01N 21/33* (2013.01); *G01N 2201/061* (2013.01); *G01N 2201/068* (2013.01)

(58) Field of Classification Search
CPC ........ G01N 21/33; G01N 21/03; G01N 1/405; G01N 2223/307
See application file for complete search history.

(56) References Cited

U.S. PATENT DOCUMENTS

| | | | | |
|---|---|---|---|---|
| 6,219,138 | B1 * | 4/2001 | Swanson | G01N 15/0205 250/575 |
| 2007/0206203 | A1 * | 9/2007 | Trainer | G01B 11/08 356/521 |
| 2009/0140168 | A1 * | 6/2009 | Goehde | G01N 15/1436 250/483.1 |
| 2016/0202164 | A1 * | 7/2016 | Trainer | G01N 15/0211 356/336 |

* cited by examiner

*Primary Examiner* — Kara E Geisel
*Assistant Examiner* — Maurice Smith
(74) *Attorney, Agent, or Firm* — Juan Carlos A. Marquez; Marquez IP Law Office, PLLC

(57) ABSTRACT

The present invention discloses a quantitative micro-volume nucleic acids detection device, which includes a light source, a first shielding screen, a second shielding screen, a lower glass plate, an upper glass plate and at least one sensor, wherein a pin-hole on the second shielding screen generates an image of a nucleic acid sample solution fixed between the bottom and upper glasses, the image is then captured by the sensor, concentration of the nucleic acid sample solution is determined accordingly. With the implementation of the present invention, the detection is reproducible and repetitive, the detection optical path is invariant, avoid of interfering from the pollution during detection so that the cost and time are greatly reduced. Furthermore, in order to overcome the measurement accuracy problem caused from attenuation of light intensity by the prolonged usage of fiber-optic components equipped in the prior art means, it avoid the use of fiber-optic components in the optical path via the present invention.

20 Claims, 5 Drawing Sheets

QUANTITATIVE MICRO-VOLUME NUCLEIC ACID DETECTION DEVICE

BACKGROUND OF THE INVENTION

1. Technical Field

The present invention relates to a quantitative detection device for measuring the concentration of a sample solution and more particularly to a quantitative micro-volume nucleic acid detection device having a first shielding screen, a second shielding screen, a lower glass plate, and an upper glass plate.

2. Description of Related Art

Conventionally, the concentration of a sample solution is measured by the Beer-Lambert law, also known as Beer's law, by injecting the solution into a quartz tube, projecting a light beam through the solution, measuring the transmittance of the solution over the entire spectrum with a conventional spectrophotometer, calculating the absorbance of the solution by reference to the intensity of the light, and estimating the concentration of the solution according to the relation between absorbance and concentration.

Since the major spectral range involved in the aforesaid computation is the ultraviolet band between 200 nm (nanometer) and 400 nm, the conventional methods and devices for measuring the concentration of a sample solution requires the sample solution to be placed in a quartz tube, for a tube made of other materials, such as glass, may absorb the light emitted by a light source of that particular waveband. Consequently, the conventional measuring techniques are disadvantaged by the high cost of quartz tubes. Other disadvantages include the required use of a relatively large amount of sample solution, poor repeatability (or reproducibility) of measurement, and difficulty in quartz tube cleaning.

Around 2004, a modified technique for measuring the concentration of a sample solution was proposed, in which measurement over a specific waveband is conducted by bringing an upper and a lower fiber-optic connector arm into contact with a sample solution and then pulling the arms apart through a solenoid valve to produce the desired variable optical path length.

As this prior art controls the variation of the optical path by opening and closing the solenoid valve, the mechanism is prone to collision while the two planes on which the fiber-optic connectors are respectively located draw near, and the collision may cause loosening or shifting of screws such that the optical path deviates from what is expected and therefore needs calibration. Also, this prior art tends to leave behind residues of the sample solution, which results in unrepeatable/unreproducible of the measurement problem. Furthermore, the problem which issued from attenuation of light intensity that caused by the prolonged usage of fiber-optic components may lower the accuracy of measurement.

Hence, it has been a major goal of innovation in the metrology instrument industry as well as the bio-medical instrument to develop a quantitative micro-volume nucleic acid detection device which is accurate and easy to use, which has a fixed optical path length during measurement, which does not require liquid compression respectively, which shows inventiveness by eliminating the need for calibration, which uses readily cleanable planar quartz glass plates that will not impair the repeatability/reproducibility or accuracy of measurement, and which solves the problems of the conventional micro-volume spectrophotometers while reducing the cost of measurement.

BRIEF SUMMARY OF THE INVENTION

The present invention relates to a quantitative micro-volume nucleic acid detection device which includes a light source, a first shielding screen, a second shielding screen, a lower glass plate, an upper glass plate, and at least one sensor. This quantitative micro-volume nucleic acid detection device is advantageous in that measurement of the concentration of a sample solution is repeatable and reproducible, that the device can be cleaned with ease, that contamination is prevented during measurement, that the optical path is fixed and needs no calibration, that fiber-optic components are dispensed with to avoid potential attenuation of light intensity, and that issues leading to inaccurate measurement have been resolved. Thus, the present invention significantly reduces the time and cost required for such quantitative detection.

The present invention provides a quantitative micro-volume nucleic acid detection device which includes: a light source; a first shielding screen formed of a light-blocking substance and having a light-permeable hole aligned with the center of the light source; a second shielding screen formed of a light-blocking substance, provided opposite the first shielding screen, and having a pinhole; a lower glass plate formed of a light-permeable substance and connected to the second shielding screen to cover the pinhole; an upper glass plate formed of a light-permeable substance and provided opposite the lower glass plate; and at least one sensor corresponding in position to the upper glass plate such that the upper glass plate is located between the lower glass plate and the sensor.

Implementation of the present invention at least involves the following inventive steps:

1. Repeatable/reproducible measurement of the concentration of a sample solution is made possible.

2. The two easily cleanable planar quartz glass plates, which serve to hold a sample solution in the detection area, through which the optical path passes, solve a major problem of the prior art, i.e., the contamination caused by the sample solution left in the vicinity of the fiber-optic connectors of a conventional spectrophotometer from direct contact between the fiber-optic connectors and the sample solution, wherein the contamination may seriously compromise the repeatability/reproducibility and accuracy of measurement.

3. The cost of quantitative micro-volume nucleic acid detection is reduced.

4. By fixing the distance between the glass plates, the optical path length is fixed (and there is only one optical path length). Therefore, the length of the optical path of the device does not need calibration.

5. No fiber-optic components are used, so attenuation of light intensity—an issue typical of the conventional micro-volume spectrophotometers and attributable to the aging of fiber-optic components is avoided.

The features and advantages of the present invention are detailed hereinafter with reference to the preferred embodiments. The detailed description is intended to enable a person skilled in the art to gain insight into the technical contents disclosed herein and implement the present invention accordingly. In particular, a person skilled in the art can easily understand the objects and advantages of the present invention by referring to the disclosure of the specification, the claims, and the accompanying drawings.

BRIEF DESCRIPTION OF THE SEVERAL VIEWS OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE INVENTION

Figure 1:
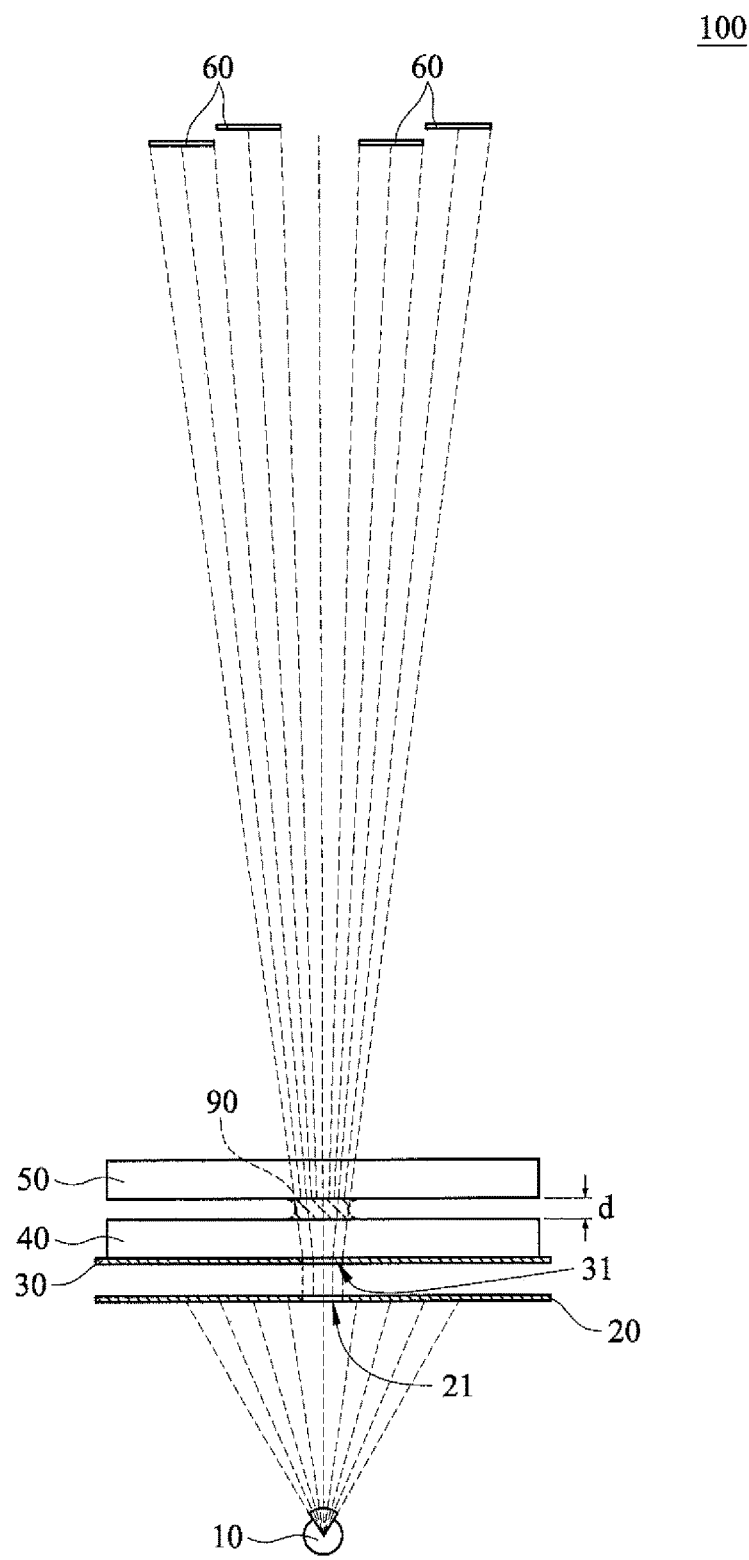
FIG. 1 is a schematic sectional view of the quantitative micro-volume nucleic acid detection device in an embodiment of the present invention.

Referring to FIG. 1, the quantitative micro-volume nucleic acid detection device 100 in an embodiment of the present invention includes a light source 10, a first shielding screen 20, a second shielding screen 30, a lower glass plate 40, an upper glass plate 50, and at least one sensor 60 with a bandpass filter configured for a specific wavelength.

Referring to FIG. 1 to FIG. 5, there are no specific limitations on the light source 10 used in the quantitative micro-volume nucleic acid detection device 100. For example, the light source 10 can be a coherent, non-coherent, or even mixed light source. There are no limitations on the wavelength of the light emitted by the light source 10, either, provided that the wavelength and intensity of the light can enable the intended measurement.

Figure 3:
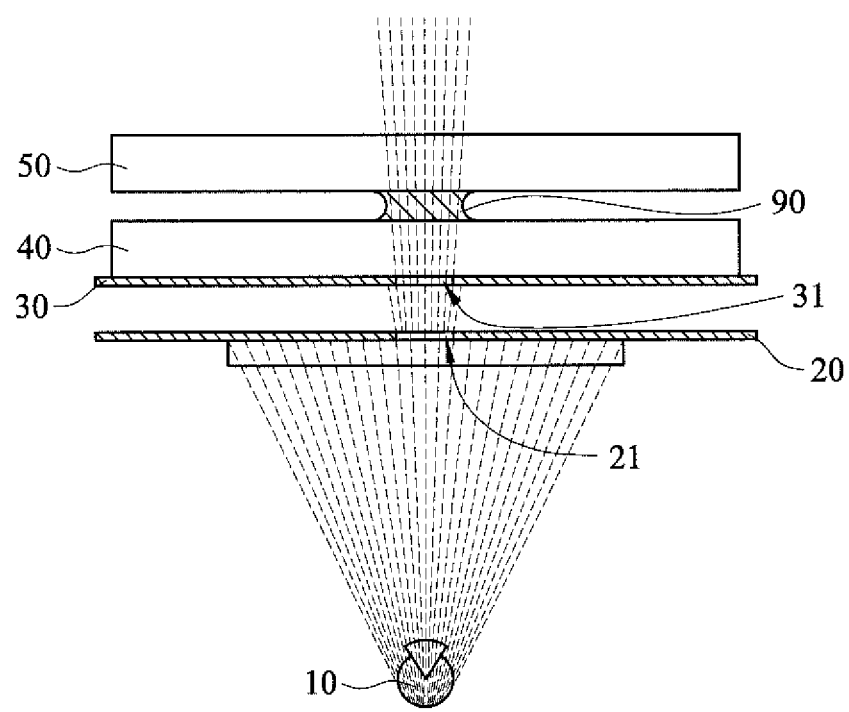
FIG. 3 is a schematic sectional view showing how the light of the light source propagates through the light-permeable hole of the first shielding screen, the pinhole of the second shielding screen, the lower glass plate, and the upper glass plate in the embodiment of FIG. 2.

As shown in FIG. 1 and FIG. 3, the first shielding screen 20 is formed of a light-blocking substance and has a light-permeable hole 21 through which a portion of the light emitted by the light source 10 can pass. The light-permeable hole 21 is aligned with the center of the light source 10.

In other words, the light source 10 is located on a line which extends from the center of the light-permeable hole 21 and which is perpendicular to the first shielding screen 20. The diameter of the light-permeable hole 21 determines the amount of light that can propagate through the light-permeable hole 21 from the light source 10. For the purpose of measurement of the present invention, the diameter of the light-permeable hole 21 in the first shielding screen 20 may range from 0.4 mm (millimeter) to 4 mm.

As shown in FIG. 1 and FIG. 3, the second shielding screen 30 is also formed of a light-blocking substance and is provided opposite the first shielding screen 20. In addition, the second shielding screen 30 has a pinhole 31 corresponding in position to the light-permeable hole 21 to ensure that light passing through the light-permeable hole 21 can reach the pinhole 31. The diameter of the pinhole 31 may range from 0.2 mm to 0.9 mm.

With continued reference to FIG. 1 and FIG. 3, the lower glass plate 40 is formed of a light-permeable substance and is connected to the second shielding screen 30 to cover the pinhole 31. Generally speaking, there are no special limitations on the thickness of the lower glass plate 40.

Referring again to FIG. 1 and FIG. 3, the upper glass plate 50 of the quantitative micro-volume nucleic acid detection device 100 is also formed of a light-permeable substance and is provided opposite the lower glass plate 40, with a glass plate spacing d defined between the upper glass plate 50 and the lower glass plate 40.

The upper glass plate 50 and the lower glass plate 40 can be provided parallel to each other such that the spacing of glass plate d between the upper glass plate 50 and the lower glass plate 40 of the quantitative micro-volume nucleic acid detection device 100 is a fixed value.

Referring to FIG. 1 to FIG. 5, a sample solution 90 to be tested is placed between the upper glass plate 50 and the lower glass plate 40 and is held between the two glass plates at a position corresponding to the pinhole 31. At this moment, the to-be-measured thickness of the sample solution 90 is fixed and is equal to the spacing of glass plate d.

In other words, by fixing the spacing of glass plate d between the upper glass plate 50 and the lower glass plate 40, the optical path length through which the quantitative micro-volume nucleic acid detection device 100 performs measurement is fixed (there is one and only one optical path length). This not only eliminates the need to calibrate the length of the optical path length of the quantitative micro-volume nucleic acid detection device 100, but also ensures that measurement is repeatable/reproducible and accurate.

The spacing of glass plate d between the upper glass plate 50 and the lower glass plate 40 may range from 0.1 mm to 0.5 mm, depending on actual measurement applications.

Referring back to FIG. 1, the at least one sensor 60 with a bandpass filter of a specific wavelength corresponds in position to the upper glass plate 50 and is located on a spatial plane that extends outward from the lower glass plate 40 through the upper glass plate 50. In other words, the at least one sensor 60 is so disposed that the upper glass plate 50 is located between the lower glass plate 40 and the at least one sensor 60.

Figure 4:
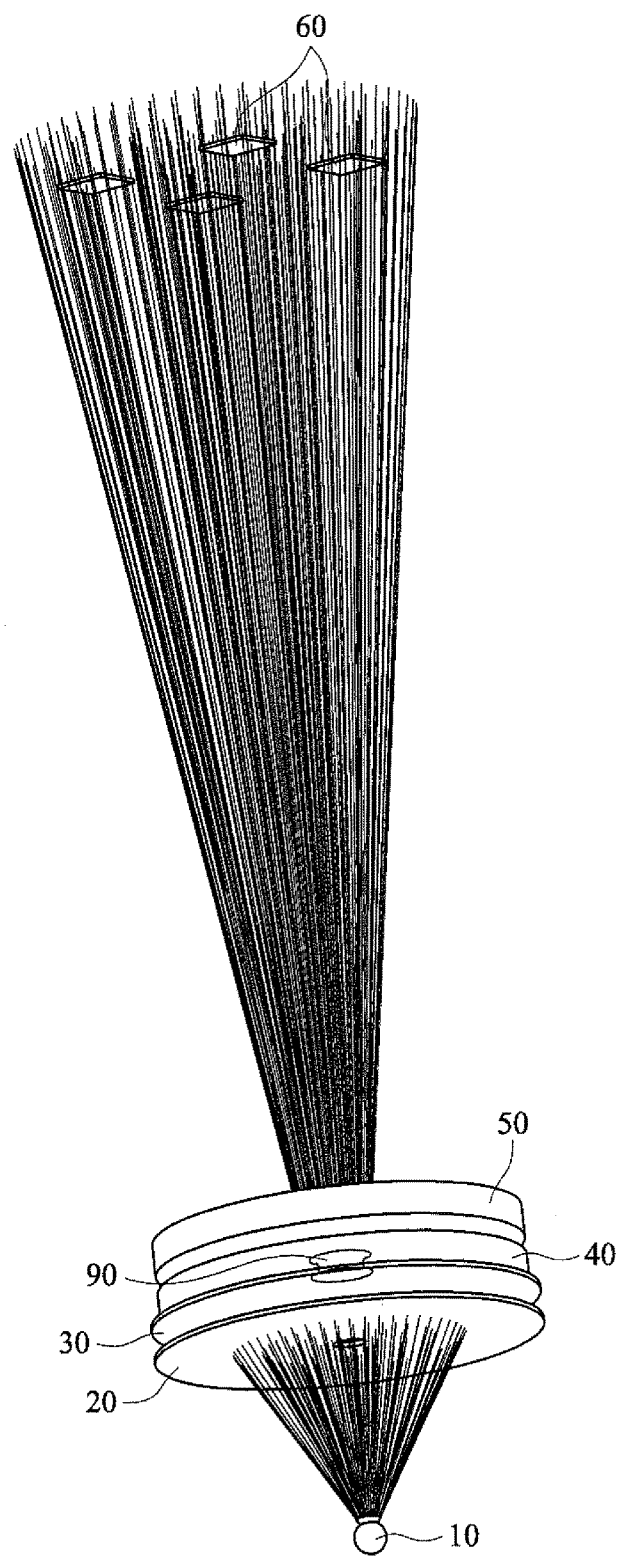
FIG. 4 schematically shows how the quantitative micro-volume nucleic acid detection device in the embodiment of FIG. 1 performs quantitative detection on a liquid.

As shown in FIG. 1 and FIG. 4, when there are two or more sensors 60, they are arranged on the same plane, and this plane is parallel to the upper glass plate 50.

The bandpass filter of the at least one sensor 60 may have a passband whose central wavelength is 230 nm (nanometer), 260 nm, 280 nm, or 320 nm.

Figure 2:
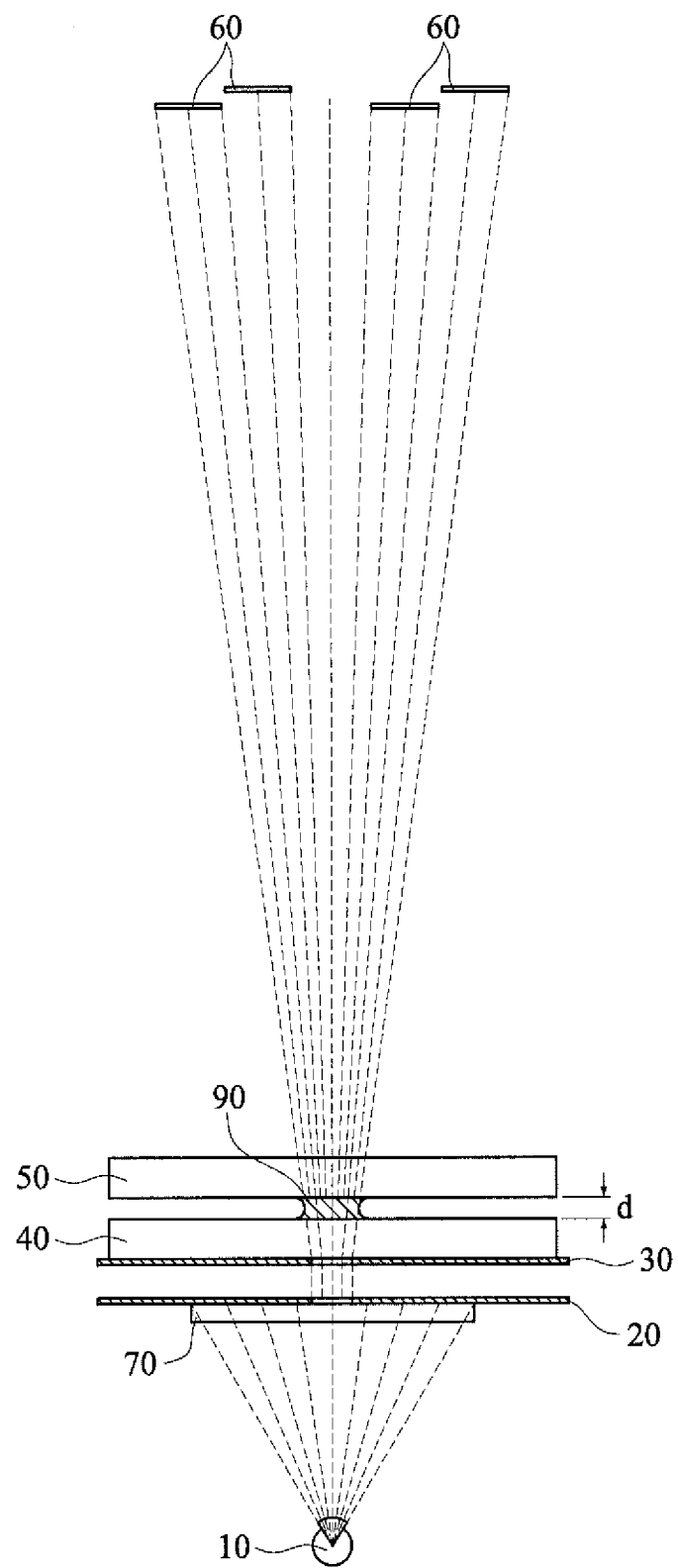
FIG. 2 is a schematic sectional view of the quantitative micro-volume nucleic acid detection device in another embodiment of the present invention.
Figure 5:
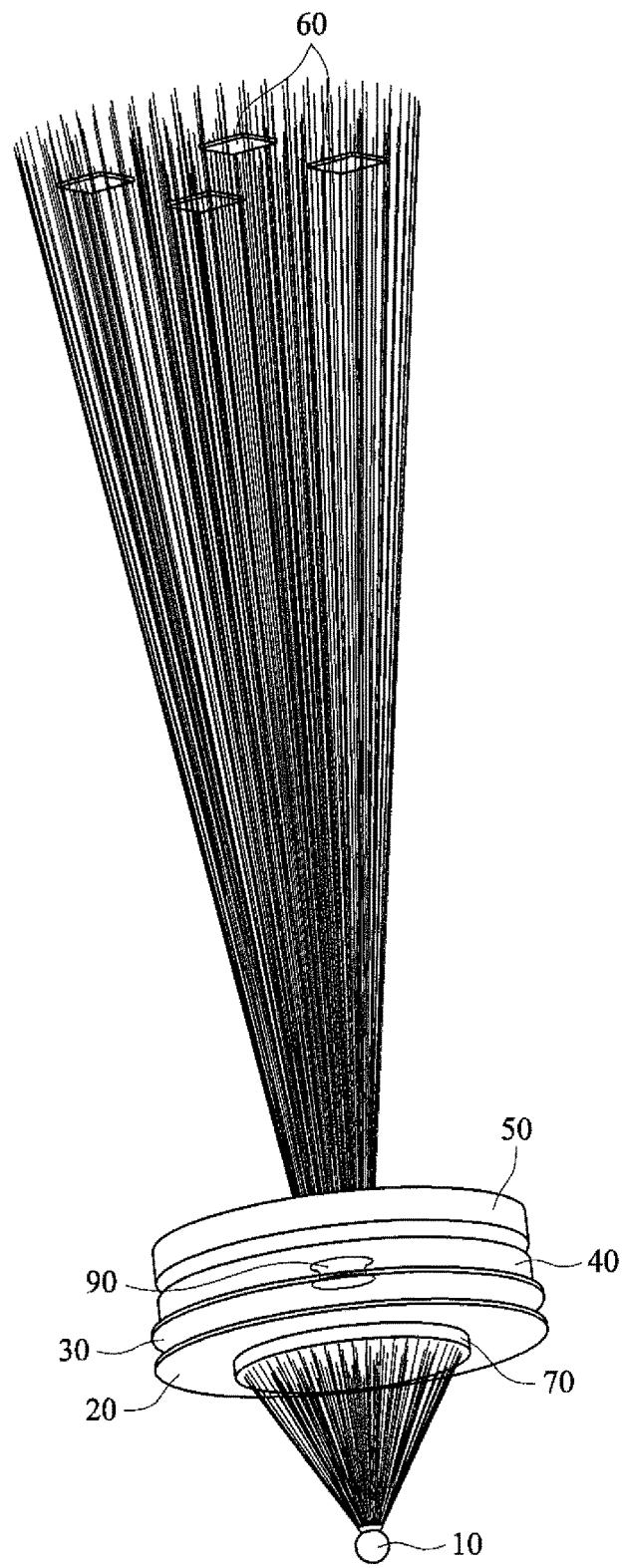
FIG. 5 schematically shows how the quantitative micro-volume nucleic acid detection device in the embodiment of FIG. 2 performs quantitative detection on a liquid.

Referring to FIG. 2 and FIG. 5, the first shielding screen 20 may be further connected with a light-enhancing glass plate 70 such that the light-enhancing glass plate 70 is located between the first shielding screen 20 and the light source 10. In addition to reinforcing the first shielding screen 20 structurally, the light-enhancing glass plate 70 may have a light-collecting effect for increasing the amount of light passing through the light-permeable hole 21.

Furthermore, the quantitative micro-volume nucleic acid detection device 100 may be connected with a power adjustment device which is electrically connected to the light source 10 to control the intensity of light emitted by the light source 10.

To measure the concentration of the sample solution 90, the quantitative micro-volume nucleic acid detection device 100 in each embodiment described above with reference to FIG. 1 to FIG. 5 works on the principle of pinhole cameras through the pinhole 31 and the at least one sensor 60 with a bandpass filter of a specific wavelength.

More specifically, a portion of the light emitted by the light source 10 propagates sequentially through the light-permeable hole 21, the pinhole 31, the lower glass plate 40, the sample solution 90, and the upper glass plate 50 to form an image on the at least one sensor 60 while the spacing of glass plate d between the upper glass plate 50 and the lower glass plate 40 remains constant.

With the two easily cleanable planar glass plates 40 and 50 retaining a sample solution in a detection area through which the optical path extends, problems associated with direct contact between the fiber-optic connectors of a conventional micro-volume spectrophotometer and a sample solution—namely the sample solution leaving hard-to-clean residues in the vicinity of the fiber-optic connectors, thereby contaminating the next sample solution to be tested and compromising the repeatability/reproducibility and accuracy of measurement—are solved.

Moreover, since the spacing of glass plate d is invariant, the length of the optical path of the quantitative micro-volume nucleic acid detection device 100 does not require calibration. The concentration of the sample solution 90 can be obtained according to the Beer-Lambert law (also referred to as Beer's law) by measuring the absorbance value of the sample solution 90 with the at least one sensor 60 and then comparing the absorbance value against a lookup table established for the device 100. The higher the absorbance, the lower the light intensity detected by the at least one sensor 60 with a bandpass filter of a specific wavelength.

The quantitative micro-volume nucleic acid detection device 100 in each of the foregoing embodiments not only reduces the cost of the intended quantitative detection, but also solves the light intensity attenuation problem of the conventional micro-volume spectrophotometers by dispensing with fiber-optic components. As previously mentioned, fiber-optic components which constitute the optical path of a conventional micro-volume spectrophotometer will age after long-term use, causing attenuation of light intensity and hence inaccurate measurement.

The embodiments described above are intended only to demonstrate the technical concept and features of the present invention so as to enable a person skilled in the art to understand and implement the contents disclosed herein. It is understood that the disclosed embodiments are not to limit the scope of the present invention. Therefore, all equivalent changes or modifications based on the concept of the present invention should be encompassed by the appended claims.

What is claimed is:

1. A quantitative micro-volume nucleic acid detection device, comprising:
   a light source;
   a first shielding screen formed of a light-blocking substance, the first shielding screen having a light-permeable hole aligned with a center of the light source;
   a second shielding screen formed of a light-blocking substance and provided opposite the first shielding screen, the second shielding screen having a pinhole;
   a lower glass plate formed of a light-permeable substance and connected to the second shielding screen to cover the pinhole;
   an upper glass plate formed of a light-permeable substance and provided opposite the lower glass plate; and
   at least one sensor having a bandpass filter of a specific wavelength, the sensor corresponding in position to the upper glass plate such that the upper glass plate is located between the lower glass plate and the sensor.

2. The quantitative micro-volume nucleic acid detection device of claim 1, wherein the light-permeable hole has a diameter ranging from 0.4 mm to 4 mm.

3. The quantitative micro-volume nucleic acid detection device of claim 1, wherein the pinhole has a diameter ranging from 0.2 mm to 0.9 mm.

4. The quantitative micro-volume nucleic acid detection device of claim 1, wherein the light-permeable hole has a diameter determining the amount of light passing through the light-permeable hole.

5. The quantitative micro-volume nucleic acid detection device of claim 1, wherein the lower glass plate and the upper glass plate are spaced by a distance ranging from 0.1 mm to 0.5 mm.

6. The quantitative micro-volume nucleic acid detection device of claim 1, wherein when there are two or more said sensors, the sensors are arranged on a same plane, and the plane is parallel to the upper glass plate.

7. The quantitative micro-volume nucleic acid detection device of claim 1, wherein the first shielding screen is further connected with a light-enhancing glass plate, and the light-enhancing glass plate is located between the first shielding screen and the light source.

8. The quantitative micro-volume nucleic acid detection device of claim 1, further comprising a power adjustment device for controlling the intensity of light emitted by the light source.

9. The quantitative micro-volume nucleic acid detection device of claim 1, wherein a portion of light emitted by the light source passes sequentially through the light-permeable hole, the pinhole, the lower glass plate, a sample solution, and the upper glass plate to form an image on the sensor.

10. The quantitative micro-volume nucleic acid detection device of claim 1, wherein the bandpass filter has a central bandpass wavelength of 230 nm (nanometer), 260 nm, 280 nm, or 320 nm.

11. The quantitative micro-volume nucleic acid detection device of claim 1, wherein a liquid is held between the lower glass plate and the upper glass plate and corresponds in position to the pinhole.

12. The quantitative micro-volume nucleic acid detection device of claim 2, wherein a liquid is held between the lower glass plate and the upper glass plate and corresponds in position to the pinhole.

13. The quantitative micro-volume nucleic acid detection device of claim 3, wherein a liquid is held between the lower glass plate and the upper glass plate and corresponds in position to the pinhole.

14. The quantitative micro-volume nucleic acid detection device of claim 4, wherein a liquid is held between the lower glass plate and the upper glass plate and corresponds in position to the pinhole.

15. The quantitative micro-volume nucleic acid detection device of claim 5, wherein a liquid is held between the lower glass plate and the upper glass plate and corresponds in position to the pinhole.

16. The quantitative micro-volume nucleic acid detection device of claim 6, wherein a liquid is held between the lower glass plate and the upper glass plate and corresponds in position to the pinhole.

17. The quantitative micro-volume nucleic acid detection device of claim 7, wherein a liquid is held between the lower glass plate and the upper glass plate and corresponds in position to the pinhole.

18. The quantitative micro-volume nucleic acid detection device of claim 8, wherein a liquid is held between the lower glass plate and the upper glass plate and corresponds in position to the pinhole.

19. The quantitative micro-volume nucleic acid detection device of claim 9, wherein a liquid is held between the lower glass plate and the upper glass plate and corresponds in position to the pinhole.

20. The quantitative micro-volume nucleic acid detection device of claim 10, wherein a liquid is held between the lower glass plate and the upper glass plate and corresponds in position to the pinhole.

\* \* \* \* \*